United States Patent [19]

Fox, Jr. et al.

[11] Patent Number: 4,581,028

[45] Date of Patent: Apr. 8, 1986

[54] INFECTION-RESISTANT MATERIALS AND METHOD OF MAKING SAME THROUGH USE OF SULFONAMIDES

[75] Inventors: Charles L. Fox, Jr., Ft. Lauderdale, Fla.; Shanta Modak, River Edge, N.J.; Keith Reemtsma, New York, N.Y.

[73] Assignee: The Trustees of Columbia University in the City of New York, New York, N.Y.

[21] Appl. No.: 605,793

[22] Filed: Apr. 30, 1984

[51] Int. Cl.$^4$ .......................... A61F 2/24; A61F 2/28; A61F 2/30; A61K 31/625

[52] U.S. Cl. .......................................... 623/2; 623/11; 623/16; 623/18; 604/265; 604/285; 128/127; 128/335.5; 424/27; 424/95; 435/1; 514/157

[58] Field of Search .......................... 424/27, 229, 95; 8/94.11; 435/1; 128/335.5, 127, 926; 604/265, 285; 3/1.4, 1.5, 1.9, 1.91

[56] References Cited

U.S. PATENT DOCUMENTS

| | | | |
|---|---|---|---|
| 3,761,590 | 9/1973 | Fox, Jr. | 424/170 |
| 3,792,161 | 2/1974 | Fox, Jr. | 424/94 |
| 4,049,802 | 9/1977 | Fox | 424/229 |
| 4,112,090 | 9/1978 | Saikawa et al. | 424/251 |
| 4,271,070 | 6/1981 | Miyata et al. | 424/27 |
| 4,287,177 | 9/1981 | Nakashima et al. | 424/81 |
| 4,292,324 | 9/1981 | Jonsson et al. | 424/145 |
| 4,353,996 | 10/1982 | Marconi et al. | 424/27 |
| 4,393,871 | 7/1983 | Vorhauer et al. | 128/127 |
| 4,401,712 | 8/1983 | Morrison | 424/27 |
| 4,404,197 | 9/1983 | Fox et al. | 424/250 |
| 4,446,124 | 5/1984 | Fox et al. | 424/27 |
| 4,455,146 | 6/1984 | Noda et al. | 424/27 |
| 4,462,981 | 7/1984 | Smith | 424/27 |

OTHER PUBLICATIONS

"Uses of Silver Sulfadiazine in Burns and Surgical Wounds", Fox, Jr., Infections in Surgery, pp. 13–22, Oct. 1982.

"Control of Burn Wound Infections by Pefloxacin and its Silver Derivative", Modak et al., Burns, 10, No. 3, pp. 170–178.

"Topical Therapy and the Development of Silver Sulfadiazine", Fox, Jr., Surgery, Gyn & Ob, 157, 82–88, Jul. 1983.

"Antibiotic Bonding to Polytetrafluoroethylene with Tridodecylmethylammonium Chloride", Harvey et al., Surgery, Sep. 1982, pp. 504–512.

"Vascular Prosthetic Infection", Bennion et al., Infections in Surgery, Sep. 1982, pp. 45–55.

"Piperacillin, A New Penicillin Active Against Many Bacteria Resistant to Other Penicillins", Fu et al., Antimicrobial Agents and Chemotherapy, 13, No. 3, pp. 358–367, Mar. 1978.

"Silver Treated Graft Material for Coverage of Infected Burn Wounds", Fox et al., Ann. Chir. Plast., 1979, 24, No. 3, pp. 265–267.

"Sulfadiazine Silver-Resistant Pseudomonas in Burns", Modak et al., Arch. Surg., 116, 854–857, Jul. 1981.

"Silver Sulfadiazine—A New Topical Therapy for Pseudomonas in Burns", Archives of Surgery, 96, pp. 184–188 (Feb. 1968).

"Virulence of Pseudomonas Infection in Burned Rats and Mice", Fox et al., Arch. Surg., 101, pp. 508–512, Oct. 1970.

"Crystal Structure of 2-Sulfanilamidopyrimidinesilver (1)", Baenziger et al., Inorganic Chemistry, 15, No. 8, pp. 1807–1809 (1976).

*Primary Examiner*—Ronald W. Griffin
*Attorney, Agent, or Firm*—Brumbaugh, Graves, Donohue & Raymond

[57] ABSTRACT

Infection-resistant materials, and methods of preparing same, suitable for use within the interior of a human or animal body in such forms as vascular grafts prostheses, or other implanted devices. The material is rendered infection-resistant by incorporating therein antimicrobial agents, such as metal salts of sulfonamides and other antimicrobials or antibacterials, such as piperacillin. In particular illustrative embodiments, silver sulfadiazine is complexed by novel techniques with natural or synthetic polymeric materials such as silk, polyester (e.g., Dacron), polyurethane, polytetrafluoroethylene, or silicone-based material, to provide long-term prevention of infections which may otherwise result during, or after, surgery or implantation of a device.

22 Claims, No Drawings

INFECTION-RESISTANT MATERIALS AND METHOD OF MAKING SAME THROUGH USE OF SULFONAMIDES

BACKGROUND OF THE INVENTION

The invention relates to the preparation of infection-resistant materials for use within the interior of a human or animal body, and more particularly, to the provision of certain antimicrobial agents into or onto polymeric materials, natural or synthetic, such as Dacron polyester, polytetrafluoroethylene, or silicone, which are usable as prostheses, grafts, implants, sutures, etc.

Infection is one of the most common complications occurring from any injury or surgical procedure. As a specific example, reconstructive surgery for patients suffering from isthemic vascular disease is now standard practice; however, vascular grafts employed in such surgery frequently develop infections, leading to serious, and often catastrophic, complications. Even with the use of perioperative antibiotics, the incidence of infection remains at about 1% to 5%. This low figure is misleading, however, for while the rate of infection is low, the morbidity and mortality associated with such infection is quite high. The mortality rate of infected aortic implant has been reported to be as high as 100 percent. Excision of an infected prosthesis is the typical treatment. In the case of infected distal grafts, the result is frequently limb loss. The problems, and known solutions, associated with vascular prosthetic infection are set forth in detail in *Infections in Surgery*, pp. 45–55, September 1982.

When infection is present prior to the operation, direct placement of a synthetic implant is often contraindicated. This could result in the need for an extra-anatomic bypass procedure, or the sacrifice of a limb. Such catastrophic complications have stimulated the search for an infection-resistant vascular prosthesis which is also compatible with biological vascular tissue.

It is known that, while vascular grafts remain susceptible to bacterial infection until the complete pseudointima has formed, graft contamination usually occurs at the time of implantation. It is difficult, if not impossible, to totally eliminate bacteria during surgical proceedings. At best, the surgeon attempts to provide a bacteriostatic environment for the graft, i.e., an environment in which the concentration of bacteria is kept at a low level by creating an environment which is hostile to bacterial growth. The attempts to limit such contamination have included application of systemic antibiotics and local irrigation with antibiotic solutions. Furthermore, the grafts are typically soaked in a solution of penicillin and heparin at the operating table immediately prior to insertion in the patient. Such attempts, however, have proven not to be completely effective, probably because of the brief residence of antibacterial agents at the implantation site. Greater success could be achieved, though, if the implantation site were kept bacteriostatic for a longer period of time.

Silver and silver compounds are recognized by those involved in fields where the prevention of infection is important, as powerful and effective bactericidal and bacteriostatic agents. Silver sulfadiazine, in particular, is known to be an excellent material for combating bacterial infection. Generally, however, the treatment of infection with silver sulfadiazine and related compounds has been approached from the standpoint of topically applying bactericidal or bacteriostatic agents in an ointment to the surface of a wound. For example, U.S. Pat. Nos. 3,761,590 and 3,792,161, the disclosures of which are herein incorporated by reference and made part of this disclosure, describe the use of silver sulfadiazine (AgSD) ointment for surface wound burn therapy.

U.S. Pat. Nos. 4,049,802 and 4,292,324, discloses zinc compounds such as zinc sulfadiazine (ZnSD), again for use in surface wound therapy. Additionally, several organic acids and their metallic salts, including silver salts, have been found to be useful in ointments for surface wound therapy. See, for example, U.S. Pat. No. 4,404,197 and U.S. patent application Ser. No. 479,029, filed Mar. 25, 1983 in the names of two of the inventors hereof, the disclosures of which are also incorporated herein by reference and made part of this disclosure. Other references also provide information on covering materials which are useful in surface wound therapy. See, e.g., U.S. Pat. No. 4,287,177 disclosing a synthetic composition suitable for use as wound coverings.

The prior art references described above all pertain to surface wound therapy. Topical application of a bactericide is not practical for an in-dwelling or surgically implanted device intended to remain in the body for a significant period of time, such as a vascular graft. Parenteral administration of antibiotics is usually unsuccessful in controlling bacterial activity at a graft or implant site because the artificial graft or implant does not have a blood supply therein. Thus, the body's natural resistance to infection is low in the graft, making it prone to infection. This problem is compounded because the circulatory system cannot transport antibiotic to the site where it is most needed. Direct incorporation of an antibiotic in the graft, however, obviates the need to rely on the circulatory system for transference of the drug. Moreover, direct incorporation places a hundred fold or greater concentration of drug at the graft site than does parenteral administration.

Application of antimicrobials at the time of insertion of the device does not solve the problem since most antimicrobial agents are rapidly absorbed into the system. However, the silver salts of certain antimicrobial agents are high molecular weight polymers (See, *Inorg. Chem.*, Vol. 15, pp. 1807–1809 (1976)) which complex with polymeric materials such as collagen, or Dacron polyester, and release silver slowly to provide antimicrobial activity for a long time. In contrast, silver applied to Dacron polyester by evaporative techniques is not inhibitory of microbial activity.

It is, therefore, an object of the invention to provide biological or synthetic materials which are compatible with body tissues, and which also prevent bacterial and microbial infection over a significant period of time.

It is further an object of the invention to provide vascular grafts, prostheses, or implants with incorporated antibacterial or antimicrobial agents, such as metal salts of sulfonamides.

It is yet a further object of the invention to provide materials for grafts, prostheses, or implants with an incorporated antibacterial or antimicrobial agent which will remain in the mateial for long-term bacteriostatic effect.

It is still a further object of the invention to provide methods of preparing synthetic vascular grafts, prostheses, or implants with incorporated antibacterial or antimicrobial agents, wherein the material comprises, inter alia, polymeric materials such as polyester, polytetrafluoroethylene, or silk.

It is yet a still further object of the invention to provide a method of treatment designed to prevent or to alleviate infections resulting from vascular surgery or implantation, comprising the employment of the polymeric materials, herein named, with antibacterial or antimicrobial agents incorporated therewith.

SUMMARY OF THE INVENTION

The foregoing and other objects are achieved by this invention wherein infection-resistant materials are provided for use within the interior of a human or animal body which comprise a polymeric substrate with a therapeutically effective amount of antibacterial or antimicrobial agents such as metal salts of sulfonamides. In a particularly advantageous embodiment, the antimicrobial agent is silver sulfadiazine. The polymeric substrate may be either natural or synthetic, examples of which are Dacron polyester, polytetrafluoroethylene, polyurethane, polyamide (Nylon), silastic or silicone, silk, umbilical cord, etc.

When the resulting product is used, for example, as graft material in vascular surgery, the treated graft materials prevent or alleviate infections. Additionally, the graft material is compatible with arterial and venous tissue, need not be examined frequently, and does not require periodic changing. Moreover, the release of drug products from the graft material proceeds at a pace conducive to long-term prevention of infection by bacterial and microbial agents.

The antibacterial or antimicrobial agents may be applied to the substrate or base material by direct incorporation from a solution or a suspension. In specific illustrative embodiments, Dacron polyester is suspended in an ammoniacal solution of 4% by weight of the agent or drug, such as silver sulfadiazine or an aqueous suspension of silver sulfadiazine to cause incorporation of the antimicrobial agent.

In an alternative embodiment, the silver salt of the organic compound, e.g., of the sulfonamide can be formed in situ on the polymeric substrate. More specifically, the substrate material is sequentially exposed to an aqueous solution of a soluble salt of the organic compound, such as a sodium salt, and to an aqueous solution of a silver salt, such as silver nitrate.

In yet another embodiment, an additional antibacterial agent, illustratively sodium piperacillin, is used in combination with the sulfonamide.

DETAILED DESCRIPTION OF THE INVENTION

Preparation of Infection-Resistant Materials

Infection-resistant materials can be prepared by novel techniques which complex an antibacterial or antimicrobial agent with a substrate material. The word "complex" is used herein to indicate some form of binding wherein the active agent is incorporated on, or with, the substrate material in such a manner to provide slow release of the active agent. The infection-resistant material is ideally suited for body-invasive uses such as for vascular grafts, heart valves, in-dwelling catheters and numerous other prosthetic or implanted devices such as intrauterine devices, sutures, etc. wherein long-term invasive contact with the body, and hence long-term prevention of infection is required.

Given below are several specific illustrative embodiments of methods of producing infection-resistant materials wherein antimicrobial or antibacterial agents are incorporated on a substrate material which may be a synthetic organic polymer such as polyester, polytetrafluoroethylene, polyurethane, nylon or silastic or other silicone-based material or a biological polymer such as collagen or silk. Although the examples given are primarily directed to the preparation of infection-resistant Dacron polyester vascular grafts prostheses, the techniques described herein are applicable to the creation of devices or implants comprising materials. The word material is used herein in its broadest sense, and can encompass, inter alia, knit or woven fabrics, single or plural filaments, extruded or molded items, etc.

The antimicrobial agents employed, are preferably, and advantageously, silver salts of sulfonamides. Sulfonamides have the general form:

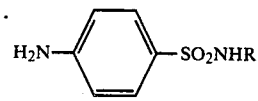

wherein R is, typically a heterocyclic organic group. A particularly advantageous, and efficacious, antimicrobial agent is 2-sulfanilamidopyrimidine silver, commonly known as silver sulfadiazine. Silver sulfadiazine, and its characteristics, are described more completely in *Surgery*, Vol. 157, pp. 82–88, July 1983, for example. Silver Sulfadiazine (AgSD), as used in the following experiments, was prepared in the inventors' laboratories, following the procedures set forth in *Arch. Surg.* 96:184 (1968).

Other antibacterial or antimicrobial agents, or a combination of agents, particularly those selected from the group of heavy metal salts (e.g., zinc salts) of sulfonamides, are within the contemplation of this invention. In particular, it was discovered that the addition of an antibacterial agent, such as sodium piperacillin, creates a synergistic effect on efficacy, particularly when combined with silver sulfadiazine.

EXAMPLE 1

Treating Grafts With A Solution Of Silver Salts

Commerically procurable Dacron polyester prosthetic vascular grafts are typically woven, knit, or velour. Samples used in experiments described herein were obtained from C. R. Bard, Inc., Implants Division, Billercia, Mass. These vascular graft samples have a diameter ranging from 6 mm for the woven variety to 8 mm for the velour.

Water-insoluble silver salts were dissolved in an ammoniacal solution. A 5 cm long piece of a Dacron polyester vascular graft was suspended in an ammoniacal solution of 4% by weight AgSD for one hour and dried in a vacuum dessicator for four hours. Then the graft was washed once with water and dried again in the vacuum dessicator. The dried graft may be stored in a refrigerator until ready for use. Just prior to use, it may be sterilized with ethylene oxide in a manner which is well known to those of skill in the art.

Moreover, it should be noted that the 4% drug concentration is given for purposes of illustration, and can be varied by those of skill in the art because it is greatly in excess of the therapeutically effective amount. Of course, other concentrations of ammonia may be either preferable or desirable. However, the ability to incorporate such high concentrations in the graft, thereby placing a high concentration of drug at the potential site of infection is a significant advantage of this invention over the prior art.

EXAMPLE 2

Treating Grafts In Aqueous Suspension Of Silver Salts

The relatively insoluble silver salts can be utilized from an aqueous suspension. In an illustrative embodiment, silver sulfadiazine containing Dacron polyester vascular grafts were prepared by cutting samples of 8 mm diameter to 5 cm in length. The pieces of Dacron were placed in an aqueous suspension containing 20 micromole AgSD per ml sterile water in an opaque tube. The tube containing the Dacron and AgSD was shaken for 24 hours. The Dacron grafts were then washed several times, covered with sterile gauze, and dried in dessicators. Prior to actual in vivo use as grafts, the Dacron polyester samples should be sterilized with ethylene oxide.

The properties of the infection-resistant Dacron polyester graft materials, prepared in the foregoing examples, are set forth below.

EXPERIMENTAL RESULTS

The concentration of silver salts incorporated on the graft materials are determined by employing radioactive samples of AgSD in the incorporation process described above. The radioactivity of these grafts was measured in a manner well known in the art to determine drug concentration. It was found that 20-30 micromoles of drug was incorporated in a 1 cm long sample of Dacron graft material.

The zone of inhibition of silver and several silver salts directly incorporated into Dacron polyester grafts was determined. Grafts were cut into 1 cm long pieces and soaked for 24 hours in suspensions of 10 micromole/ml of the silver salts AgSD and silver nitrate ($AgNO_3$). For comparative purposes, Dacron grafts of the same length were coated on both sides with silver. All grafts were rinsed twice with sterile water and then placed on blood agar plate cultures containing samples of *Pseudomonas aeruginosa* (Boston), as described in *Arch. Surgery* 101:508 (1970), or *Staphylococcus aureus*, at concentration levels of $10^4$, $10^3$, and $10^2$ organisms. The diameter of the zone of inhibition for each case is given in mm, in Table I.

TABLE I

Incorporation Using Aqueous Suspension Of Drug

| Bacteria | Concentration Of Bacteria | Zone Of Inhibition Of Drug-Treated Graft, mm | | |
|---|---|---|---|---|
| | | AgSD | $AgNO_3$ | Silver |
| *Pseudomonas* | $10^4$ | 18 | 8 | 0 |
| *Aeruginosa* | $10^3$ | 19 | 14 | 0 |
| (Boston) | $10^2$ | 28 | 20 | 0 |
| *Staphylococcus* | $10^4$ | 19 | 8 | 0 |
| *aureus* | $10^3$ | 18 | 14 | 0 |
| | $10^2$ | 18 | 15 | 0 |

The diffusion of incorporated drugs was tested on blood agar plates, nutrient broth culture, and in whole blood. The method used was identical to that used in the zone of inhibition study described above in connection with Table I. After testing for the amount of drug remaining in the treated graft on the first day, a fresh culture plate or tube was used each day for ten days. The zone of inhibition and bacterial turbidity was measured. The results of this investigation are set forth in Table II. Table II shows the release of drug from AgSD-containing Dacron in the presence of various culture media and blood by the concentration of drug remaining in the graft after exposure to the medium. A (0) indicates no turbidity, and hence, no growth. A (+) indicates bacterial growth.

TABLE II

| Days Of Incubation | Concentration Of Drug Remaining in Graft (micromole/2 mm) | | | Antibacterial Zone In Plate (mm) | Activity Turbidity In Broth |
|---|---|---|---|---|---|
| | Blood Agar Plate | Nutrient Broth | Blood | | |
| 0 | 4.0 | 4.0 | 4.0 | 25 | 0 |
| 1 | 3.2 | 3.1 | 2.7 | 22 | 0 |
| 3 | 2.8 | 2.7 | 2.5 | 22 | 0 |
| 4 | 2.7 | 2.5 | 1.8 | 22 | 0 |
| 5 | 2.3 | 2.3 | 0.9 | | 0 |
| 6 | 2.2 | 2.2 | 0.8 | | 0 |

The inhibitory effect of Dacron polyester grafts including different antibacterial agents was tested. Graft materials were prepared as indicated in the examples above, and were then soaked in 5 ml of nutrient broth containing the bacteria *Pseudomonas aeruginosa* (Boston), or *Staphylococcus aureus*, at various concentration levels. These samples were then incubated for 24 to 48 hours, and observed for growth of bacteria. For purposes of comparison, elemental silver (Ag) was coated on Dacron graft material. The results are given in Table III, wherein a (+) indicates growth of bacteria, where a (−) indicates absence of growth.

TABLE III

| Bacteria | Concentration | Antibacterial Agents | | |
|---|---|---|---|---|
| | | AgSD | $AgNO_3$ | Ag |
| *Pseudomonas* | $10^6$ | + | + | + |
| *aeruginosa* | $10^4$ | − | + | + |
| | $10^3$ | − | − | + |
| *Staphylococcus* | $10^6$ | − | − | + |
| *aureus* | $10^4$ | − | − | + |
| | $10^3$ | − | − | + |

In a particularly advantageous embodiment of the invention, the metal salt of the organic compound can be formed in situ on the substrate material. The following Examples 3, 4, and 9 illustrate this technique.

EXAMPLE 3

In Situ Formation Of Silver Salts

This procedure can be utilized with any of the aforementioned materials, irrespective of whether the material is synthetic or natural. For the purpose of illustration, Dacron polyester, PTFE, and rubber or silicone-containing Foley catheter materials were treated to render them infection-resistant.

Samples of these materials were placed in an aqueous solution of a soluble sulfonamide salt, illustratively a 30 micromole solution of sodium sulfadiazine, for a period of about an hour. The samples were removed from the solution and blotted dry. Then, the samples were placed in aqueous solution of a soluble silver salt such as silver nitrate for a period of time sufficient to allow reaction between the sulfadiazine salt and the metal salt so as to produce the metal salt of sulfadiazine in, or on, the sample. In the actual tests performed, a period of about five to ten minutes was found to be sufficient.

The thus-treated samples were washed vigorously in water, dried for about an hour, and then stored in a dark place until use. The samples can be sterilized by means, well known in the art, prior to use in vivo.

The in situ technique for incorporating a metal salt of a sulfonamide has several advantages. It is believed that the freshly precipitated metal salt intercalates the substrate better and yet releases more gradually. We have also found that the therapeutically effective concentration of the antimicrobial agent is less for the in situ technique. Moreover, since the salts are water soluble, delicate biological tissue, such as porcine heart valves, can be safely treated by the method of Example 3.

It should be noted, however, that the solvent for the organic and metal salts does not have to be water. The choice of another solvent is well within the skill of one of ordinary skill in the art. It should further be noted that while silver is particularly effective, other metals, such as zinc, can be used to create the antimicrobial agents. A specific example of a known non-silver complexed antimicrobial agent is zinc sulfadiazine.

EXPERIMENTAL RESULTS

The concentration of silver salts incorporated on the sample materials by the in situ technique of Example 3 was determined by employing radioactive samples of silver nitrate in the in situ reaction. The radioactivity of the samples was measured in a manner well known in the art. The results are set forth in Table IV wherein the concentration of silver subsequent to preparation of the sample is shown in column (A).

1 cm long samples of Dacron polyester vascular graft material were suspended in tubes containing 5 ml of a culture medium comprising nutrient broth in a known concentration of bacteria. The tubes containing the samples were incubated for 24 hours. The results of this experiment for concentrations of *Staphylococcus aureus* on the order of $10^5$, $10^6$, and $10^7$ organisms are given in Table IV. A sample of the broth from each tube was cultured on a blood agar plate and incubated in order to defect bacterial growth. The results are indicated on Table IV as a plus (+) for growth and a minus (−) for no growth.

The in vitro activity of the samples was further tested by measuring the zone of inhibition, in mm, by standard disc inhibition studies on a blood agar plate according to techniques described above. The concentration of silver was again measured after the disc inhibition studies and is given in column (B) of Table IV.

TABLE IV

| DRUG CONTENT AND IN VITRO ACTIVITY OF GRAFTS | | | | |
|---|---|---|---|---|
| (A) Silver (micromole) | (B) Silver (micromole) | Antibacterial Activity | | |
| | | Concentration Of Bacteria | Growth In Tube | Zone In Plate (mm) |
| AgSD | | | | |
| 10–12 | 5–8 | $10^5$ | − | 15–18 |
| 10–12 | 5–8 | $10^6$ | − | 15–18 |
| 10–12 | 5–8 | $10^7$ | + | 15–18 |

EXAMPLE 4

In a specific advantageous embodiment of the in situ technique for producing infection-resistant materials, vaginal sponges were treated to incorporate silver sulfadiazine.

Vaginal sponges are being widely accepted as a means of contraception or as a means of administering medications to the female vaginal cavity and cervix due to the ability of the sponge to provide long-term retention and slow release of medicaments. Typically, vaginal sponges comprise an expandable polymer, such as polyurethane. If used as a means of contraception, a well known spermicide, such as Nonoxynol-9 is included in the polymeric sponge. U.S. Pat. No. 4,393,871 provides a detailed description of a vaginal sponge device wherein the sponge is formed by mixing a polyurethane prepolymer with an aqueous solution of Nonoxynol-9 which acts as a surfactant, or foaming agent, during formation of the polymeric sponge, and as a spermicide in the final device. In addition to the spermicide Nonoxynol-9, U.S. Pat. No. 4,393,871 also suggests that other drugs, or medicaments, can be added to the polyurethane prepolymer.

We have discovered that Nonoxynol-9 exhibits very little infection resistance. Silver Sulfadiazine, on the other hand, is extremely effective at killing a wide spectrum of microorganisms. In particular, silver sulfadiazine is lethal to venereal disease producing organisms such as *Treponea pallida,* Gonococcus, *Staphalococcus aureus*-coagulate positive, *Candida albicans* and *Herpes hominus.* Moreover, the addition of silver sulfadiazine may prevent toxic shock syndrome. While not as effective as Nonoxynol-9, silver sulfadiazine also exhibits some spermicidal activity. Thus, incorporation of silver sulfadiazine in a vaginal sponge would have many beneficial effects.

Pieces of commercially procured vaginal sponges weighing 600 mg were placed in an aqueous 120 millimole solution of sodium sulfadiazine for about an hour. The pieces were blotted to remove excess fluid and then suspended in an aqueous 100 millimole solution of silver nitrate for about five minutes. Again, the excess fluid was blotted off and the sponge pieces were dried in a vacuum dessicator for about an hour. The sponge pieces were washed with sterile water and then dried again.

Pieces of vaginal sponge weighing 20 mg apiece and containing about 3 micromole of silver sulfadiazine, were placed in nutrient broth containing various concentrations of bacteria and then a sample of the broth was tested for bacterial growth. The results are given in TABLE V as a plus (+) for growth and a minus (−) for no growth. Sponge samples were also placed in Sabouraud broth to test anti-fungal properties against various concentrations of *Candida albicans.* None of the cultures containing treated sponges exhibited bacterial, or fungal, growth. On the other hand, all of the cultures from control samples of untreated vaginal sponges, containing only Nonoxynol-9, exhibited heavy bacterial growth.

TABLE V

| Antibacterial Effect of AgSD Impregnated Sponge | | | | |
|---|---|---|---|---|
| | STERILITY OF CULTURES (concentration of bacterial) | | | |
| ORGANISM | $10^7$ | $10^6$ | $10^5$ | $10^4$ |
| *Pseudomonas aeruginosa* | − | − | − | − |
| *Staph. aureus (FID)* | − | − | − | − |
| *Staph. aureus (Harlem)* | − | − | − | − |
| *Staph. epidermidis* | − | − | − | − |
| *Eschechia coli* | − | − | − | − |
| *Klebsiella pneumonia* | − | − | − | − |
| *Candida albicans* | − | − | − | − |

Several miscellaneous examples of specific devices, rendered infection-resistant by application of the techniques set forth herein, are given below in Example 5–8.

EXAMPLE 5

It has been discovered that the strings on intrauterine devices permit bacteria to travel into the uterus and Fallopian tubes. These strings can be provided with an antimicrobial agent by treating a polymeric filament, such as nylon, or a plurality of such filaments comprising the string, in accordance with the methods of Examples 1-3. Vaginal sponges are typically provided with a ribbon loop to aid in their removal, these too, can be treated to render them infection-resistant. Tampons, and other internal feminine hygiene products, can likewise be treated. The toxic shock syndrome prevention ability of AgSD, in particular, renders such treatment advisable.

In a similar manner, surgical sutures can be rendered infection resistant. It is well known that the presence of a foreign body decreases the body's natural resistance to infection; thereby lowering the concentration of organisms required to start an infection. It is known that a single silk suture can potentiate *Staphylococcus aureus* as much as ten thousandfold. *Ann N.Y. Acad. Sci.*, Vol. 65, pp. 85-90, 1956. Thus, treatment of sutures by the methods described herein could be of great benefit.

EXAMPLE 6

Another useful material for vascular grafts, inter alia, is the polymer, polytetrafluoroethylene (PTFE), also known as Teflon. The method of incorporation must be varied for PTFE material to cause adherence of the drug to a surface coating of gelatin or albumin or a surfactant such as sodium dodecyl sulfate or benzalkonium chloride. Improving vascular integrity by simple coating procedures is known in the art (Grode, G. A. et al., *Trans. Am. Soc. Artificial Internal Organs*, Vol. 15, p. 106, (1969)). Therefore, the coatings are typically prepared by the manufacturer. The surfactant produces a smoother suface which has an anti-thrombogenic effect and produces a further advantage in that it aids adherence of the antibacterial agent to the suface of the graft. Another advantageous surfactant for coating PTFE is tridodecyl methyl ammonium chloride as described in *Surgery*, Vol. 92, No. 3, pp. 504-512, (1982). Coated PTFE can be treated in accordance with the illustrative methods set forth in Examples 1, 2, 3, and 9. It should be noted, however, that the aforementioned coatings produce advantageous results on other materials, such as Dacron polyester.

EXAMPLE 7

For incorporating antimicrobials into biological tissue, such as procine heart valves, the ammoniacal solution should be diluted with water to prevent damage to the tissue. In an illustrative embodiment, the 4% active drug in ammonium hydroxide solution is diluted with water to produce a solution containing about 0.1 to 0.4% active drug. In an alternative embodiment, an aqueous suspension of the active drug may be used to incorporate antimicrobials into delicate biological tissue. However, the method of Example 3 may be best suited for this purpose.

EXAMPLE 8

In-dwelling Foley catheters require frequent changing to prevent bacteria from traveling along the catheter tube into the bladder. This procedure is both time consuming for the doctor and painful for the patient. Therefore, providing a bacteriostatic catheter tube would obviate the need for frequent changing. Samples of natural rubber and silicone-containing catheters, such as obtainable from C. R. Bard, Inc., Urological Div., Murray Hill, N.J., were prepared by methods analogous to the above-discussed techniques.

Pieces of the catheter (3 mm in length) were soaked in a solution containing 4% AgSD in ammonia for 2 hours, removed, rinsed, dried and tested for antibacterial activity by disc inhibition studies. A zone of inhibition measuring approximately 17 mm in diameter on blood agar culture was obtained.

EXAMPLE 9

In a further specific illustrative embodiment, an additional antibacterial agent is included in the in situ incorporation technique. In a specific embodiment, sodium piperacillin was found to produce a synergistic effect on antimicrobial action in combination with silver sulfadiazine.

As shown above, silver sulfadiazine-treated Dacron prosthetic vacular grafts were quite effective against *Staphylococcus aureus, E. coli* and *Pseud. aeruginosa* when treated in vitro using nutrient broth as the culture medium. However, when the AgSD-treated grafts were tested in a culture medium containing human blood, the grafts were less effective. This is possibly the result of rapid binding of the drug to blood proteins which reduces the amount of drug available to inhibit bacterial growth. The test data shown in Tables VII and VIII prove the synergistic effect of the combination of, illustratively, AgSD and sodium piperacillin against both gram negative and gram positive bacteria.

Piperacillin is a semisynthetic piperazine penicillin derivative having the structural formula:

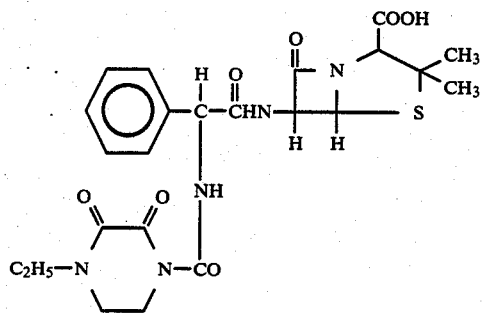

The sodium salt of piperacillin is commonly known as Pipracil. Pipracil is a trademark of Lederle Laboratories, Pearl River, N.Y. A more complete disclosure of the nature of sodium piperacillin and related compounds can be found in U.S. Pat. No. 4,112,090; in particular, see Compound 36 at Col. 65.

In a specific illustrative technique, Dacron polyester vascular prosthetic graft samples were used as the substrate material. The samples were placed in a solution containing about 30 millimoles of Pipracil and 80 millimoles of sodium sulfadiazine for about an hour. Then the samples were blotted dry and placed in a second solution containing 30 millimoles of silver nitrate for five to ten minutes. This procedure creates AgSD in situ. An alternate embodiment, the samples can be placed in an aqueous suspension of AgSD containing Pipracil. The treated samples are then washed with sterile water and dried under a vacuum in a dessicator.

EXPERIMENTAL RESULTS

The antibacterial activity of vascular prosthetic grafts treated with AgSD and AgSD and Pipracil (PPR) was compared by placing samples of each type of treated graft in nutrient broth and in a medium containing 50% nutrient broth and 50% blood. Various concentrations of bacterial organisms, in this case, Staph. aureus were placed in the media and incubated. The results are shown in Table VI wherein a minus (−) indicates no growth and a plus (+) indicates growth on a blood agar plate innoculated with a specimen of the media. The amount of bacterial growth is ranked by the number of bacterial colonies grown wherein 0-5 is (−), 5-20 is (+), 20-50 is (2+), 50-100 is (3+), and greater than 100 is a (4+).

TABLE VI

| Bacteria Concentration | Nutrient Broth | | Medium Containing 50% Blood | |
|---|---|---|---|---|
| | AgSD | AgSD + PPR | AgSD | AgSD + PPR |
| $10^4$ | − | − | 3+ | − |
| $10^5$ | − | − | 4+ | − |
| $10^7$ | − | − | 4+ | 3+ |

The synergistic effect of the combination of silver sulfadiazine is shown in Table VII wherein various concentrations of AgSD, PPR, and combinations of AgSD+PPR were placed in tubes containing a nutrient broth medium and a $10^4$ concentration of Pseud. aerugi-nosa (Boston). The tubes were incubated and examined for turbidity. A zero (0) indicates no turbidity and a plus (+) indicates visible turbidity.

TABLE VII

| COMPOUNDS | Concentration of Drug (nanomoles/ml) | | | | |
|---|---|---|---|---|---|
| AgSD | 100 | 50 | 25 | 12.5 | 6.0 |
| Growth | 0 | 0 | + | + | + |
| PPR | 500 | 250 | 125 | 60 | 30 |
| Growth | 0 | 0 | + | + | + |
| AgSD + | 12.5 | 12.5 | 12.5 | 12.5 | 12.5 |
| PPR | 60.0 | 30.0 | 15.0 | 7.5 | 3.75 |
| Growth | 0 | 0 | 0 | 0 | 0 |
| AgSD + | 6.0 | 6.0 | 6.0 | 6.0 | 6.0 |
| PPR | 60.0 | 30.0 | 15.0 | 7.5 | 1.0 |
| Growth | 0 | 0 | 0 | 0 | + |

The combination of silver sulfadiazine and sodium piperacillin also exhibits a synergistic effect on a variety of organisms as shown in Table VIII. Various concentrations of AgSD, PPR, and combinations thereof were placed in tubes containing a nutrient broth medium and a $10^4$ concentration of various organisms. The tubes were incubated and examined for turbidity. As usual, a zero (0) indicates no turbidity and a plus (+) indicates visible turbidity. The vertical line in Table VIII separates the results for AgSD and PPR per se from the results for a mixture of the two. This strikingly demonstrates the superior efficacy of AgSD and PPR together. It should be noted that the concentrations of AgSD and PPR, which are effective in combination, are significantly lower than the inhibitory concentration for each agent alone.

TABLE VIII

Antibacterial Spectrum Of Silver Sulfadiazine and Piperacillin

| ORGANISM | Drug | Concentration (nanomole/ml) | | | | | | |
|---|---|---|---|---|---|---|---|---|
| Staphylococcus aureus (47-1) | AgSD | 3 | 0 | 3 | 3 | 1.5 | .7 | .7 |
| | PPR | 0 | 6 | 6 | 3 | 6 | 6 | 3 |
| | Growth | + | + | 0 | 0 | 0 | 0 | + |
| Klebsiella pneumoniae | AgSD | 3 | 0 | 3 | 3 | 1.5 | | .7 |
| | PPR | 0 | 6 | 6 | 3 | 3 | | 3 |
| | Growth | + | + | 0 | 0 | 0 | | 0 |
| Eschericia coli | AgSD | .7 | 0 | .7 | .7 | .7 | | .7 |
| | PPR | 0 | .7 | .7 | .35 | .18 | | .09 |
| | Growth | + | + | 0 | 0 | 0 | | 0 |
| Proteus vulgaris | AgSD | 1.5 | 0 | 1.5 | 1.5 | 1.5 | .7 | .7 | .7 |
| | PPR | 0 | .35 | .35 | .18 | .09 | .35 | .18 | .09 |
| | Growth | + | + | 0 | 0 | 0 | 0 | 0 | 0 |

The foregoing examples and experimental results were given for the purpose of illustration only and are not to be construed as limiting the scope of the invention. Numerous and varied examples of the application of the principles of the invention can be devised by those of skill in the art without departing from the spirit and scope of the invention. In particular, other antibacterial or antimicrobial agents can be incorporated on the grafts in accordance with the methods described above. Moreover, the examples cited do not preclude the use of other known material engineering techniques, such as pre-swelling of the substrate, or inclusion of the antimicrobial agent in a pre-polymer, to achieve the goal of long-term incorporation of antimicrobial agents from materials.

Other substrate materials, such as umbilical cords or collagen can be substituted for the materials specifically named herein. It is also to be understood that the term polymer is to be construed to include copolymer. Any variations required in the procedure would be well within the ordinary skill of the person of skill in the art.

Furthermore, the type of device to which this invention is applicable is not limited to those specifically mentioned; other examples include skin buttons, synthetic heart valves, sutures, the components of intrauterine device, bone and joint replacements, cannulas, pacemakers, vascular access devices for hemodialysis, cosmetic implants of silicone, etc.

What is claimed is:

1. A method for reducing the risk of infection by bacteria as a result of prosthetic vascular graft surgery, said method comprising the use of a vascular graft comprising a polymeric substrate provided with an effective amount of at least one antimicrobial agent selected from the group consisting of metal salts of sulfonamdies.

2. A method for reducing the risk of infection by bacteria as a result of a device implanted within the interior of a human animal body, said method comprising the use of an implanted device which comprises a polymeric substrate provided with an effective amount of at least one antimicrobial agent selected from the group consisting of metal salts of sulfonamides for at least a portion of the implanted device.

3. An infection-resistant device which is a vascular graft prosthesis for use within the interior of a human or animal body wherein at least a portion of said vascular graft prosthesis comprises a polymeric substrate provided with an effective amount of at least one antimicrobial agent selected from the group consisting of metal salts of sulfonamides.

4. An infection-resistant device which is a catheter for use within the interior of a human or animal body wherein at least a portion of said catheter comprises a polymeric substrate provided with an effective amount of at least one antimicrobial agent selected from the group consisting of metal salts of sulfonamides.

5. An infection-resistant device which is an internal contraceptive device for use within the interior of a human or animal body wherein at least a portion of said internal contraceptive device comprises a polymeric substrate provided with an effective amount of at least one antimicrobial agent selected from the group consisting of metal salts of sulfonamides.

6. An infection-resistant device which is an internal feminine hygiene device for use within the interior of a human or animal body wherein at least a portion of said internal feminine hygiene device comprises a polymeric substrate provided with an effective amount of at least one antimicrobial agent selected from the group consisting of metal salts of sulfonamides.

7. An infection-resistant device which is a surgical suture for use within the interior of a human or animal body wherein at least a portion of said surgical suture comprises a polymeric substrate provided with an effective amount of at least one antimicrobial agent selected from the group consisting of metal salts of sulfonamides.

8. An infection-resistant device which is a vaginal sponge for use within the interior of a human or animal body wherein at least a portion of said vaginal sponge comprises a polymeric substrate provided with an effective amount of at least one antimicrobial agent selected from the group consisting of metal salts of sulfonamides.

9. An infection-resistant device which is a heart valve for use within the interior of a human or animal body wherein at least a portion of said heart valve comprises a polymeric substrate provided with an effective amount of at least one antimicrobial agent selected from the group consisting of metal salts of sulfonamides.

10. An infection-resistant device which is a cannula for use within the interior of a human or animal body wherein at least a portion of said cannular comprises a polymeric substrate provided with an effective amount of at least one antimicrobial agent selected from the group consisting of metal salts of sulfonamides.

11. An infection-resistant device which is a cosmetic implant for use within the interior of a human or animal body wherein at least a portion of said cosmetic implant comprises a polymeric substrate provided with an effective amount of at least one antimicrobial agent selected from the group consisting of metal salts of sulfonamides.

12. An infection-resistant device which is a bone or joint replacement for use within the interior of a human or animal body wherein at least a portion of said bone or joint replacement comprises a polymeric substrate provided with an effective amount of at least one antimicrobial agent selected from the group consisting of metal salts of sulfonamides.

13. The infection-resistant device of any one of claims 3-12 wherein said polymeric substrate comprises synthetic polymeric material.

14. The infection-resistant device of claim 13 wherein said synthetic polymeric material is selected from the group consisting of polyester, polytetrafluoroethylene, polyurethane and polyamide.

15. The infection-resistant device of claim 14 wherein said synthetic polymeric material is a polyester.

16. The infection-resistant device of claim 13 wherein said synthetic polymeric material is silicone.

17. The infection-resistant device of any one of claim 3-12 wherein said polymeric substrate comprises a natural polymeric material.

18. The infection-resistant device of claim 17 wherein said natural polymeric material is selected from the group consisting of collagenous substances, biological tissues and silk.

19. The infection-resistant device of any one of claims 3-12 wherein said at least one antimicrobial agent comprises a silver salt of a sulfonamide.

20. The infection-resistant device of claim 19 wherein said at least one antimicrobial agent comprises silver sulfadiazine.

21. The infection-resistant device of claim 20 wherein said at least one antimicrobial agent further includes an antibacterial agent.

22. The infection-resistant device of claim 21 wherein said at least one antibacterial agent is sodium piperacillin.

* * * * *

UNITED STATES PATENT AND TRADEMARK OFFICE
CERTIFICATE OF CORRECTION

PATENT NO.  : 4,581,028
DATED       : April 8, 1986
INVENTOR(S) : Charles L. Fox, Jr., et al It is certified that error appears in the above-identified patent and that said Letters Patent is hereby corrected as shown below:

Col. 2, line 7, "discloses" should read -- disclose --.
Col. 4, line 11, "material" (not in quotation marks) should read -- "material" --; line 50, "Billercia" should read -- Billerica --. Col. 6, line 30, "where" should read -- while --. Col. 7, line 39, "defect" should read -- detect --. Col. 10, line 22, "vacular" should read -- vascular --. Col. 12, line 41, "device" should read -- devices --; line 50, "sulfonamdies" should read -- sulfonamides --. Col. 13, line 38, "cannular" should read -- cannula --. Col. 14, line 13, delete "one"; line 24, "any one of claim" should read -- any of claims --; line 31, delete "one".

Signed and Sealed this

Twenty-third Day of September 1986

[SEAL]

Attest:

DONALD J. QUIGG

Attesting Officer

Commissioner of Patents and Trademarks